United States Patent
Goldman et al.

(10) Patent No.: US 12,280,212 B2
(45) Date of Patent: Apr. 22, 2025

(54) METHOD AND APPARATUS FOR SIMULTANEOUSLY ADMINISTERING OXYGEN, AND METERED DOSE INHALER MEDICATION BY INHALATION

(71) Applicants: Peter Goldman, Allentown, PA (US); Michael Newhouse, Hamilton (CA)

(72) Inventors: Peter Goldman, Allentown, PA (US); Michael Newhouse, Hamilton (CA)

(*) Notice: Subject to any disclaimer, the term of this patent is extended or adjusted under 35 U.S.C. 154(b) by 840 days.

(21) Appl. No.: 17/594,989

(22) PCT Filed: Apr. 30, 2020

(86) PCT No.: PCT/US2020/030811
§ 371 (c)(1),
(2) Date: Nov. 4, 2021

(87) PCT Pub. No.: WO2020/227024
PCT Pub. Date: Nov. 12, 2020

(65) Prior Publication Data
US 2022/0347421 A1    Nov. 3, 2022

Related U.S. Application Data

(60) Provisional application No. 62/843,480, filed on May 5, 2019.

(51) Int. Cl.
*A61M 16/08* (2006.01)
*A61M 15/00* (2006.01)
*A61M 16/06* (2006.01)

(52) U.S. Cl.
CPC ...... *A61M 16/0875* (2013.01); *A61M 15/009* (2013.01); *A61M 16/06* (2013.01); *A61M 2202/0208* (2013.01)

(58) Field of Classification Search
CPC ............ A61M 15/0021; A61M 15/009; A61M 15/0086
See application file for complete search history.

(56) References Cited

U.S. PATENT DOCUMENTS 5,701,886 A    12/1997  Ryatt
5,954,049 A *  9/1999  Foley ................... A61D 7/04
                                          128/203.29
(Continued)

FOREIGN PATENT DOCUMENTS

AU    2020268815 B2    12/2022
CA    3138181 C         7/2022
(Continued)

OTHER PUBLICATIONS

International Search Report and Written Opinion for PCT/US2020/030811, mailing date of Aug. 13, 2020.

*Primary Examiner* — Kendra D Carter
*Assistant Examiner* — Jaeick Jang
(74) *Attorney, Agent, or Firm* — Rivkin Radler LLP

(57) ABSTRACT

An apparatus and method are provided for administering an inhaled drug to a person while simultaneously administering oxygen from a medical oxygen mask. The inhaled drug is from a pressurized metered dose inhaler (MDI), employing an extender tube about 3-10 cm long that fits into or over the mouthpiece of the inhaler. The MDI with extender tube is inserted into the mask and positioned so that the plume of drug travels through the extender when the MDI is actuated and is directed to just inside the mouth of the person. In an embodiment, an exhalation filter is provided to prevent contamination from infectious agents in the exhaled air from the person.

9 Claims, 9 Drawing Sheets

(56) References Cited

U.S. PATENT DOCUMENTS

| | | |
|---|---|---|
| 6,595,204 B2 | 7/2003 | Genova et al. |
| 7,832,395 B2 | 11/2010 | Rogers |
| 8,464,715 B2 | 6/2013 | Flynn |
| 9,186,474 B1 | 11/2015 | Rollins, III |
| 9,272,108 B2 | 3/2016 | Hu |
| 9,498,592 B2 | 11/2016 | Dhuper et al. |
| 2005/0028811 A1* | 2/2005 | Nelson ................ A61M 16/107 128/200.11 |
| 2008/0078382 A1 | 4/2008 | LeMahieu |
| 2008/0210242 A1 | 9/2008 | Burk et al. |
| 2012/0216806 A1 | 8/2012 | Rookard et al. |
| 2014/0283837 A1 | 9/2014 | Turrisi |
| 2016/0158477 A1 | 6/2016 | Dupher et al. |
| 2017/0173291 A1 | 6/2017 | Pedro et al. |
| 2018/0133417 A1 | 5/2018 | Krishna et al. |

FOREIGN PATENT DOCUMENTS

| | | |
|---|---|---|
| EP | 3956001 B1 | 6/2023 |
| IN | 543217 B | 6/2024 |
| WO | WO2008116165 A9 | 9/2008 |
| WO | WO2013158738 A1 | 10/2013 |
| WO | WO2019023300 A1 | 1/2019 |

\* cited by examiner

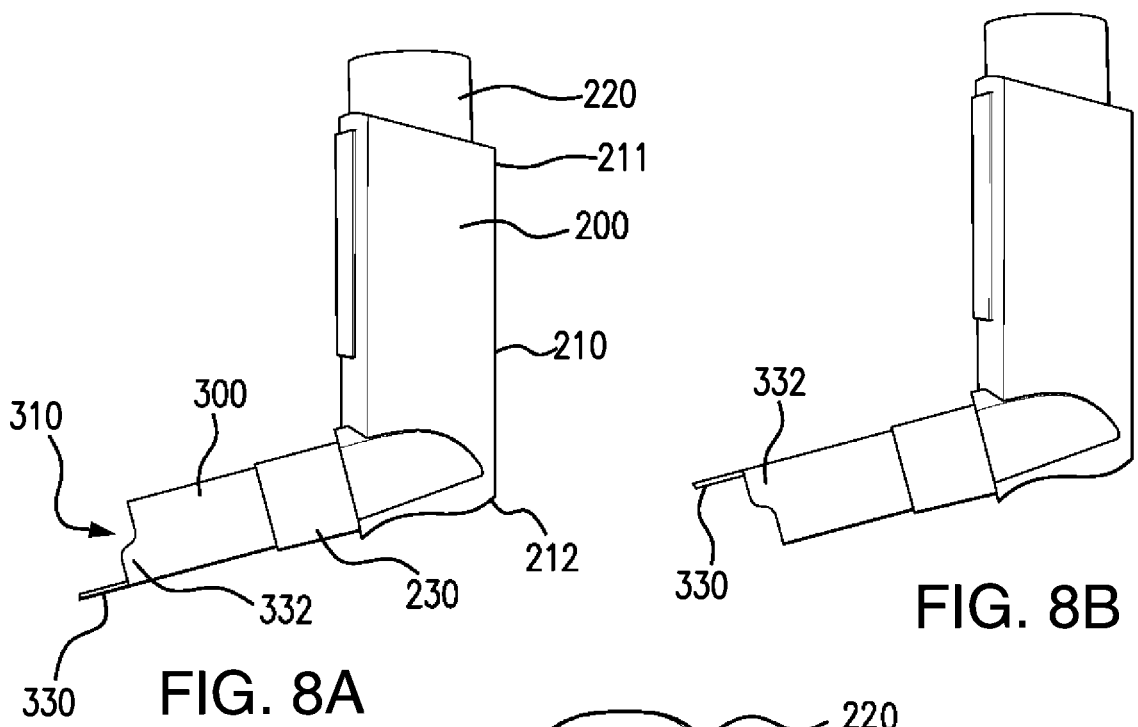
FIG. 8A
FIG. 8B
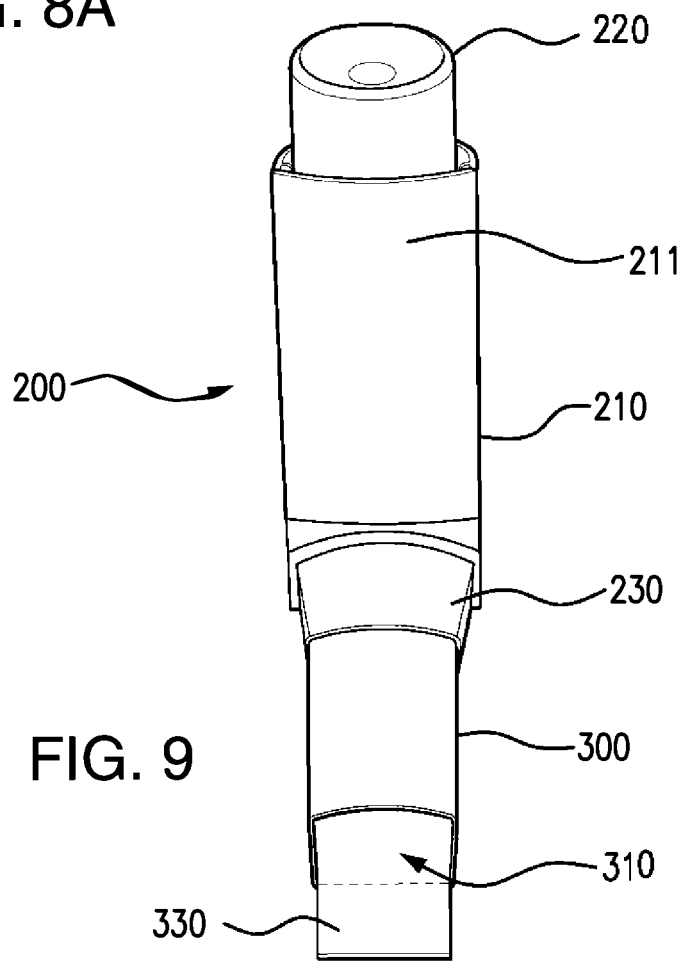
FIG. 9

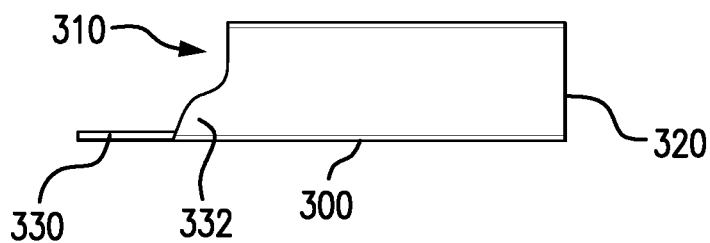
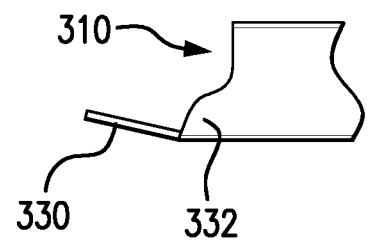
FIG. 10A  FIG. 10B
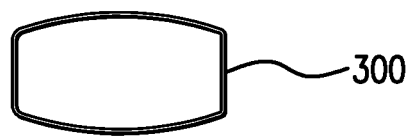
FIG. 11
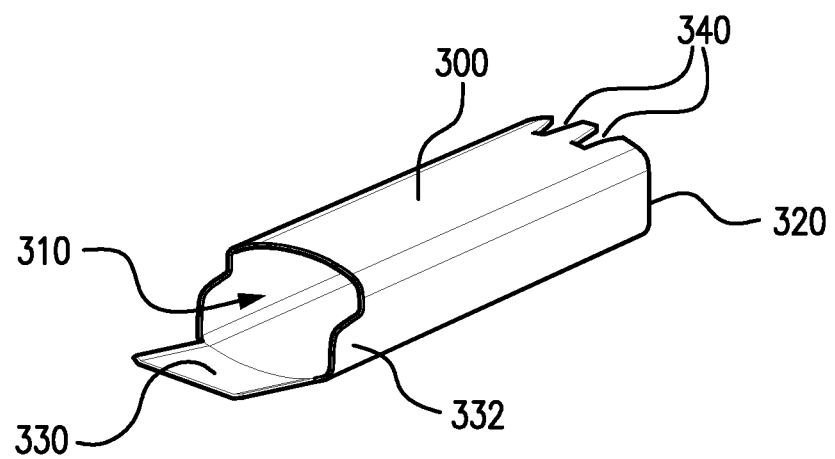
FIG. 12

METHOD AND APPARATUS FOR SIMULTANEOUSLY ADMINISTERING OXYGEN, AND METERED DOSE INHALER MEDICATION BY INHALATION

CROSS REFERENCE TO RELATED APPLICATION

This application is the National Stage entry under 35 U.S.C. § 371 of PCT patent application PCT/US20/30811, filed Apr. 30 2020, which claims priority to U.S. Patent Application 62/843,480 filed May 5, 2019, the contents of each of which are incorporated by reference.

FIELD OF THE INVENTION

The invention provides a method and apparatus for administering aerosol medications such as beta adrenergics, sympathomimetics, anticholinergics, and corticosteroids, or a combination thereof, from a metered dose inhaler (MDI) through an oxygen delivery mask. The invention provides for the simultaneous administering of aerosol medication and oxygen, which is often beneficial in the context of emergency response, or maintenance treatment of significant respiratory disorders.

BACKGROUND

There is a great need for a simple to operate device or system that would simultaneously, rapidly, and reliably provide oxygen, inhaled bronchodilator, and other medication such as corticosteroids, for instance, to patients with airflow obstruction due to exacerbations of bronchospasm, mucosal edema and/or excess mucus resulting from airway inflammation due to, among others, asthma, chronic obstructive pulmonary disease (COPD), cystic fibrosis, physical or chemical inhalation injury, etc. These inhaled medications are conveniently transported and administered to patients with a pressurized metered dose inhaler (MDI).

However, effective MDI use requires the patient to coordinate breathing with the administration of the drug by depressing the MDI during inhalation. This is not possible with unconscious or incompetent patients, including small children. Two approaches to this problem have been developed: valved holding chambers and nebulizers. Up to now, no effective method has been described to administer a drug with an MDI while simultaneously administering oxygen with an oxygen mask. This feature may be desirable, for example, in an emergency situation in the field or in a hospital setting.

A shortcoming with the use of valved-holding-chambers (VHC) and high dose albuterol, which is now used frequently in many countries for emergency response, is that the oxygen mask must be removed while administering the bronchodilator aerosol. This is inconvenient and time consuming as the therapist must alternate the oxygen mask and the VHC mask to provide oxygen and medication to the patient, and this results in no supplemental oxygen during medication administration and potential hypoxemia. An alternative is to use nasal oxygen, but approximately ⅔ of asthmatics in distress have associated obstructed nostrils.

In the United States aerosols are commonly administered in medical/hospital situations through small-volume-nebulizers (SVNs). SVNs have several shortcomings. One problem is that the air or oxygen flow in an SVN is limited to a narrow range of about 6-8 L/min. At times this can be an insufficient oxygen flow for treating severe exacerbations of, for example asthma and/or associated pneumonia, often treated in hospital emergency departments. At the same time, there is considerable concern for hyperoxemia, or excessive oxygen in the bloodstream caused by excess oxygen administration, resulting in worse outcomes. Frequently, less than 6-8 L/min flow is required for adequate oxygenation of a patient, and at times up to 15 L/min is required. If the oxygen flow to a SVN however is lowered, the rate of nebulization is proportionately lowered and the aerosol particle size may be adversely increased. As a result, the duration of therapy may become very lengthy and aerosol dose to the lung greatly reduced. If the flow is increased above 8-10 L/min, the output becomes progressively more ineffective due to the formation of large droplets and concomitant less effective aerosol delivery ("spitting"). Another shortcoming is that SVNs in hospital emergency situations must be set up, which is somewhat time consuming, and very often tasked to an on-call respiratory therapist, adding a delay in administration, as well as adding additional labor in the response. As a result, the patient's improvement may be delayed.

The device of the instant invention allows complete dissociation of oxygen flow from the aerosol medication delivery, which allows for the administering of adequate oxygen concentration to the patient along with the provision of high dose multiple (8-12) puffs of albuterol in a matter of 3-4 minutes, as opposed to at least three times that for an equivalent dose from an SVN, as an example.

The inventors found that simultaneous administration of MDI bronchodilators thru a port or orifice into an oxygen mask at 2-15 L/min oxygen flow for relief of acute asthma and/or COPD exacerbations proved to be particularly difficult due to the "wash-out" of the bronchodilator(s) by the incoming oxygen flow into the mask. The relatively high flow oxygen jet disperses the drug aerosol initially expressed into the mask from the MDI that was inserted into the mask, and as a result, much of the drug is dispersed around the interior of the mask and is washed out of the mask and back out through the MDI housing to ambient by the flow of oxygen, rather than being inhaled by the patient. Measured blood levels of the albuterol drug provided as such were shown to be negligible.

Certain types of oxygen masks (hereinafter termed "CPR masks") in common use, particularly for First Aid and EMS use, have a one-way valve fitted into a 22 mm porthole in the center of the mask's dome, and an oxygen inlet below. The one-way valve permits rescue breaths from an emergency first responder to enter the mask. Alternatively, a bag-valve ventilation device can be attached in its place to administer air or supplemental oxygen when available. When used, the one-way valve prevents back flow from the patient to minimize exposure of bodily fluids and exhaled breath to emergency responders. Examples of such masks include the "Ambu® Res-Cue Mask", "EverGuard CPR Pocket Mask," and the "Curaplex® CPR Pocket Mask." There are many others. In all of them, the one-way valve is readily removable, and can be reinserted if needed for rescue breathing in exhausted or apneic patients.

Other types of oxygen delivery masks widely in use in hospital emergency departments and on the inpatient floors and in emergency medical services (EMS) that could be used with the invention are the simple rebreather mask, the non-rebreather mask (NRB), the partial rebreather mask and the Southmedic OxyMask™. The simple rebreather, partial rebreather and NRB would require a porthole similar to the CPR mask to be created or manufactured-in, for insertion of the inventive MDI-extender tube. The OxyMask however already has suitable orifices, as manufactured. Additionally, any other oxygen mask with an orifice in its dome that is large enough for full insertion and aiming of the extender tube, could be used.

SUMMARY OF THE INVENTION

The present invention provides a solution to the problem of administering inhaled medications from an MDI while simultaneously administering oxygen, without either effecting the delivery of the other. When a CPR mask is used to deliver oxygen, this is accomplished by removing the one-way valve in the front of the mask and replacing it by e.g., an albuterol MDI mouthpiece equipped with an inventive extender tube. This allows supply of oxygen up to 15 L/min from an oxygen source, and simultaneous bronchodilator MDI aerosol administration by expressing the aerosol puff thru the extender tube with its tip just within the open mouth of the patient, at the time of their inhalation.

This invention addresses the incompatibility of simultaneous oxygen administration and use of a VHC, and the complexity and limitations of oxygen flow using an SVN, which can be driven by relatively narrow range of oxygen flow. An SVN can be used with oxygen therapy but takes significant time to set up, is cumbersome to use in emergency situations compared to the invention, and for adequate aerosol medication delivery it is dependent on a narrow range of oxygen flow rates which are often not the optimal flow rate for the patient.

One object of the invention is to provide for an apparatus with minimum number of components which is easy to use and clean, inexpensive if disposable, and economical to manufacture. Another object of the invention is to provide for a simple and rapid method for simultaneously and precisely oxygenating the patient and rapidly providing aerosol medication. The disclosed apparatus is easy to operate, which makes it especially convenient for treating acute asthma and/or COPD exacerbations by lay first aid providers using first aid oxygen units, emergency medical services personnel (EMS) at the scene and in ambulances, in the hospital emergency department (ED), on hospital wards, and in the home by caregivers. The disclosed apparatus allows emergency medical technicians (EMTs)/paramedics and ED personnel to respond quickly and more efficiently, as it can be placed on the patient and be operative within 30-60 seconds vs the ~5 mins required to setup and load the SVN and initiate treatment. An additional objective of the invention is to reduce the time for completion of bronchodilator therapy in an emergency, therefore providing for more rapid patient improvement, which would allow patients to continue their recovery at home or on a hospital ward rather than remaining in the ED for longer periods or requiring transfer to ICU, which will result in considerable potential cost saving.

In an embodiment, an apparatus is provided for administering medication through inhalation from a metered dose inhaler (MDI) to a patient using an oxygen delivery mask after the mask is in place delivering oxygen, without removing the oxygen mask or interrupting the flow of simultaneous oxygen delivery to the patient.

In an embodiment, an extender tube is provided for a metered dose inhaler (MDI) apparatus that provides an aerosolized medication, comprising a hollow body about 3-10 cm long, with a cross section that matches the profile of the mouthpiece of the MDI, wherein the extender tube has a proximal end in fluid contact with the MDI, wherein the proximal end fits snugly into or over the MDI mouthpiece such that the aerosolized medication plume from the MDI, when activated, is directed into the tube, and a distal end wherein the tube directs the flow of the aerosolized medication to just inside the open mouth of a patient in need of the aerosolized medication. In an embodiment, the extender tube is about 5-6 cm long.

In an embodiment, an apparatus is provided for the administering an inhaled drug to a person from a pressurized metered dose inhaler (MDI). The apparatus includes an MDI having a body, a mouthpiece section, a canister containing a drug for inhalation, wherein the canister contains an actuator mechanism that permits a predetermined dose of drug to be released from the mouthpiece section when actuated, and wherein by pressing downward on the canister in relation to the base of the body, the canister is actuated to release a predetermined dose of the drug as an aerosol plume through the mouthpiece section of the inhaler. The apparatus further includes an extender tube about 3-10 cm long that fits snugly into or over the mouthpiece of the inhaler such that the plume of drug travels through the extender when the canister is actuated. The extender tube is inserted into the interior of an oxygen mask through an opening in the oxygen mask The extender tube has a distal opening end for the patient opposite the proximal opening end for the metered dose inhaler mouthpiece. The patient end of the extender tube is positioned within the oxygen mask such that its tip is just within the mouth of the patient, so that when the patient's mouth is open, the aerosol plume is directed into the mouth of the patient. In an embodiment, the extender tube is about 5-6 cm long.

In an embodiment, the oxygen mask is selected as a CPR mask having a one-way valve, a rebreather mask, or an OxyMask™.

In an embodiment, the oxygen mask is a CPR mask and the one-way valve is removed and the mouthpiece section of the body of the metered dose inhaler is inserted into the porthole in mask for the one-way valve.

In an embodiment, a method is provided for administering an inhaled medication to a person from a pressurized metered dose inhaler, comprising the apparatus described above, wherein the person's mouth is open at the time the metered dose inhaler is actuated, and wherein the person inhales at approximately the same time, to deliver the aerosol plume dose of the drug to the lungs of the person.

In an embodiment, the apparatus and method further includes an exhalation filter that traps infectious agents, wherein the filter is nested in a distal end of a flexible sleeve, wherein a proximal end of the flexible sleeve is nested over the body of an MDI, such that an exhalation air pathway is created through the MDI housing and the exhaled breath passes through the exhalation filter. The exhalation filter may include a housing with a proximal edge, and the sleeve attaching it to the inhaler is sufficiently flexible to permit pushing the filter housing down towards the canister in the MDI with sufficient force to actuate the MDI.

BRIEF DESCRIPTION OF THE DRAWINGS

FIG. 8A is a side elevation view of the MDI apparatus and extender tube, before insertion into a mask, showing the deflector flap on the bottom of the extender tube.

FIG. 8B is a side elevation view of the MDI apparatus and extender tube, before insertion into a mask, showing the deflector flap on the top of the extender tube.

FIG. 9 is a perspective view from the top of the MDI apparatus and extender tube, not inserted into a mask.

FIG. 10A is a side view of the extender tube in a non-flexed position. FIG. 10B is a is a side view of the extender tube with the deflector flap flexed upward.

FIG. 11 is a view down the longitudinal axis of the of the extender tube, showing an exemplary cross section.

FIG. 12 is a perspective view of an embodiment of the extender tube with a scoop-like profile at the patient end of the extender tube and two notches at the proximal end for clearance of the MDI mechanics when inserted into an MDI mouthpiece.

DETAILED DESCRIPTION

Figure 1:
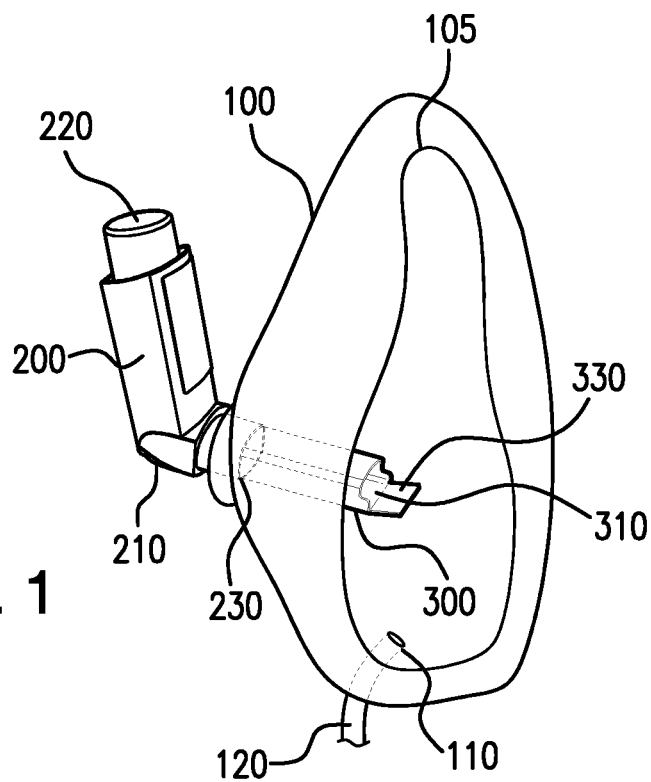
FIG. 1 is a perspective view of the apparatus according to an embodiment of the present invention, utilizing a CPR oxygen mask.

The disclosure provides for an apparatus and a method for administering inhaled aerosol medications to a patient, such as beta adrenergics, sympathomimetics, anticholinergics, and corticosteroids, or a combination thereof, from a pressurized metered dose inhaler (MDI). The apparatus is useful with any of various common styles of oxygen masks and allows simultaneous administration of the aerosolized medication with medical oxygen, without removing the oxygen mask or interrupting the flow of oxygen while the medication is administered. Several exemplary oxygen masks are illustrated herein. In an embodiment, this invention is useful in the emergency administration of inhaled bronchodilator medications as rescue therapy for patients in respiratory distress, such as during an asthma attack. This device allows the administration of an inhaled bronchodilator with simultaneous oxygen administration. In an embodiment, this invention may also be used in non-emergency situations in a hospital setting.

In this invention, an extender tube 300 (FIG. 12) is provided that can be inserted into or over the mouthpiece section 230 of an MDI body (FIGS. 8A, 8B, and 9). In an embodiment, the extender tube is a hollow body about 3-10 cm long, with a cross section (FIG. 11) that matches the profile of the mouthpiece of the MDI, wherein the extender tube has a proximal end 320 connected to the MDI and a distal end 310, wherein the proximal end fits snugly into or over the MDI mouthpiece such that the aerosolized medication plume from the MDI, when activated, is directed into the tube, and the tube thereby directs the flow of the aerosolized medication into the open mouth of a patient receiving the medication. The tube is inserted into an oxygen mask as provided herein and allows for the efficient administration of inhaled drugs from an MDI while the patient is wearing the oxygen mask and inhaling breathing gases enriched with oxygen. This use of the tube to channel the inhalable medication from an MDI to the mouth of the patient addresses the problem noted above that simply inserting an MDI mouthpiece into a mask with a flow of oxygen causes "wash-out" of the drug, i.e., the drug aerosol or particles (i.e., the discharge from an MDI) are dispersed within the mask and out to ambient, and as a result measured drug levels inhaled by the patient are very low. In the instant invention, measured drug levels of the MDI drug in the lung are high.

References to the length of the extender tube do not include flap 330 (FIGS. 10 and 12). In an embodiment, the tube may be 5-6 cm long. The precise length is generally not critical as long as the tube when inserted into a mask and MDI can reach the mouth of the patient even if the MDI is pressed up to the mask. In some mask styles, longer or shorter tubes may be required or may be easier to work with. Most of the mask styles discussed herein are flexible, but generally, it is not a problem if the MDI protrudes a few centimeters from the mask.

The tube may fit into or over the mouthpiece 230 of an MDI. The drawings illustrate this with the tube inside the mouthpiece.

By the term "about" used herein with a measurement, this is meant to be ±20% of the stated value. The terms "proximal" and "distal" are position indicators relative to the elbow 212 of an MDI. The terms "patient" and "person" are used interchangeably.

Figure 13:
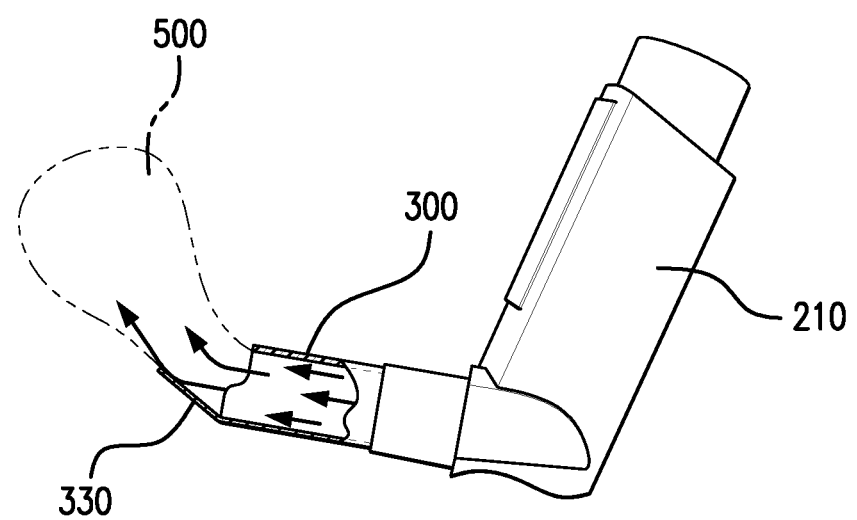
FIG. 13 shows a cutaway view of the inventive extender in operation, showing the flap flexed about 30° to deflect the aerosol plume.

FIG. 12 shows an embodiment of the invention with the lower rim of the distal end of the extender tube having a scoop, or lip, 332 and a flexible flap 330. Flap 330 can be used to direct the flow of the plume of aerosolized medication, typically either up or down. Depending on the nature of the oxygen mask, it may desirable to direct the plume up or down so that the plume of aerosolized medication is directed into and parallel the open mouth of the patient. With certain oxygen mask styles and varied facial geometries, the ability to direct the plume in this fashion can be a critical factor in directing the plume into the mouth of the patient. Thus, in the extender tube with a flexible flap, the plume of aerosolized medication after activation of the MDI will be directed opposite flap 330, as shown in FIG. 13, with flap on the bottom side of the extender and the aerosol plume directed upward. Because of the symmetry in the cross section of the MDI mouthpiece, the extender tube can be removed, rotated 180°, and replaced into the MDI mouthpiece so the direction of the plume can be reversed to the opposite direction (FIGS. 8A and 8B).

Figure 5:
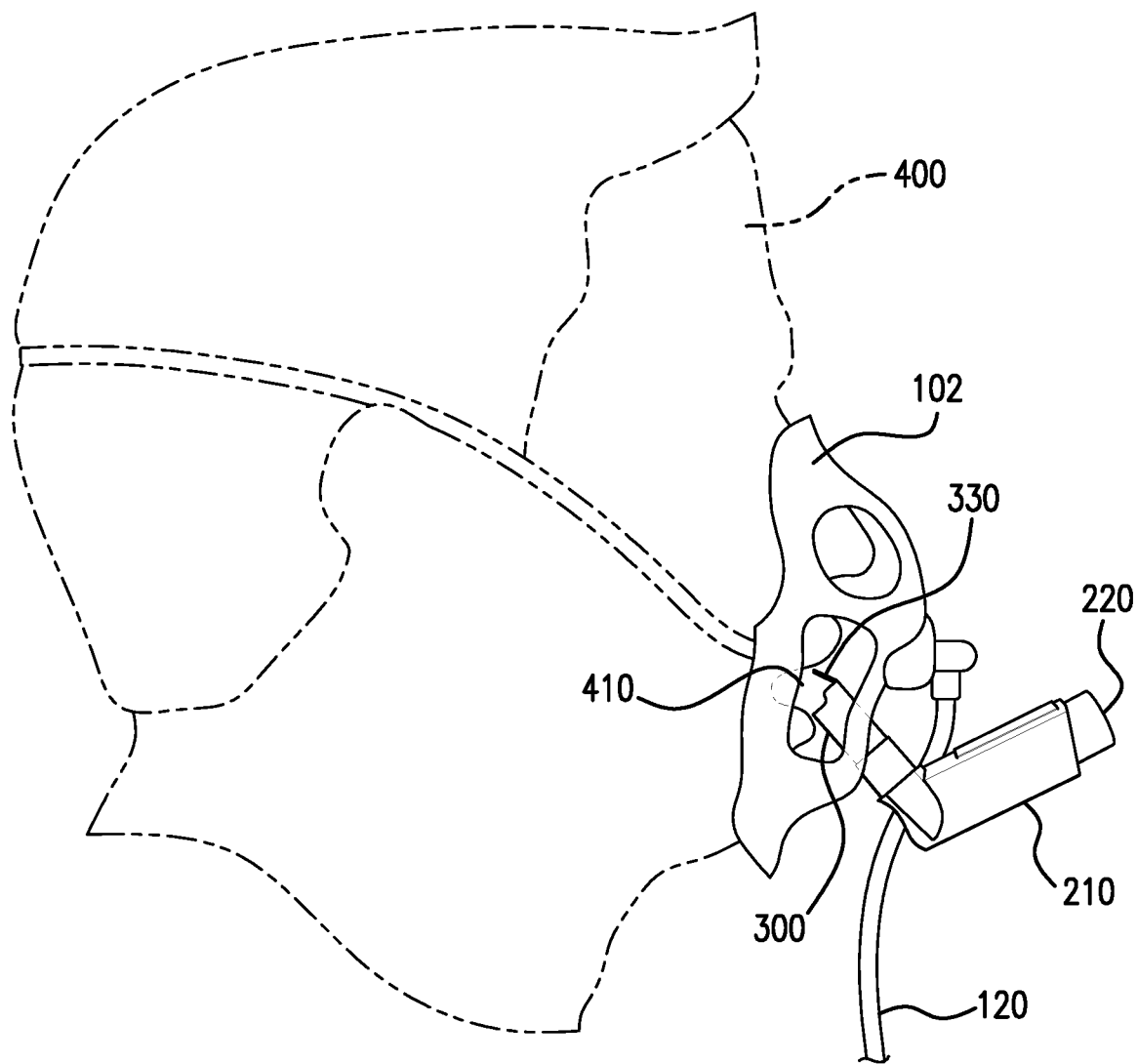
FIG. 5 is a side view of a "Southmedic OxyMask™ on the face of a patient, showing the relationship of the extender tube to the mouth of the patient.

In an embodiment, the flap 330 is flexible and can flex up to about 30°, but as shown in FIG. 10A, without pressure on the flap, it remains in a neutral unflexed position in-line with the longitudinal axis of the extender tube 300. In another embodiment, the flap 330 may be flexed by contact with the upper or lower lip (as the case may be). This is shown in FIG. 5, where the flap 330 is in contact with the upper lip of the patient to cause a downward flexion as compared to the neutral position of the flap shown in FIG. 8B. FIG. 10B is an elevation view showing the flap 330 flexed. In an embodiment, the flap pressed against the lip may flex by up to about 30° to direct the plume of aerosol medication as required.

FIGS. 8A, 8B, and 9 illustrate the extender 300 inserted into MDI mouthpiece 230. In use, the aerosolized medication plume from the MDI is directed into the extender tube that is directed at the mouth of the patient. See e.g., FIGS. 2, 4, and 5. This device is intended for use by persons in respiratory distress, such as an acute asthma attack, so the patient will normally have an open mouth (patients suffering an acute asthma attack almost always open their mouths for easier breathing). Thus, the plume of aerosolized medication will be directed some distance away from the MDI apparatus and into the patient's mouth.

Figure 2:
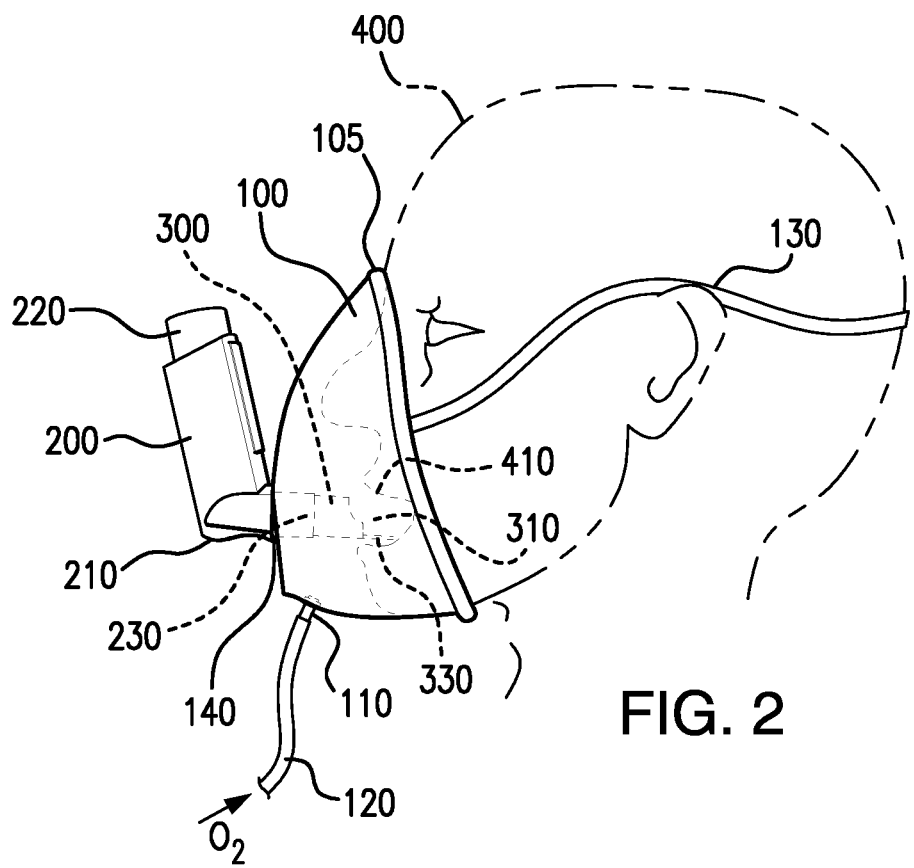
FIG. 2 is an elevation of the apparatus from the side, showing the interaction of the MDI, extender tube, and mask with a patient with an open mouth.
Figure 3:
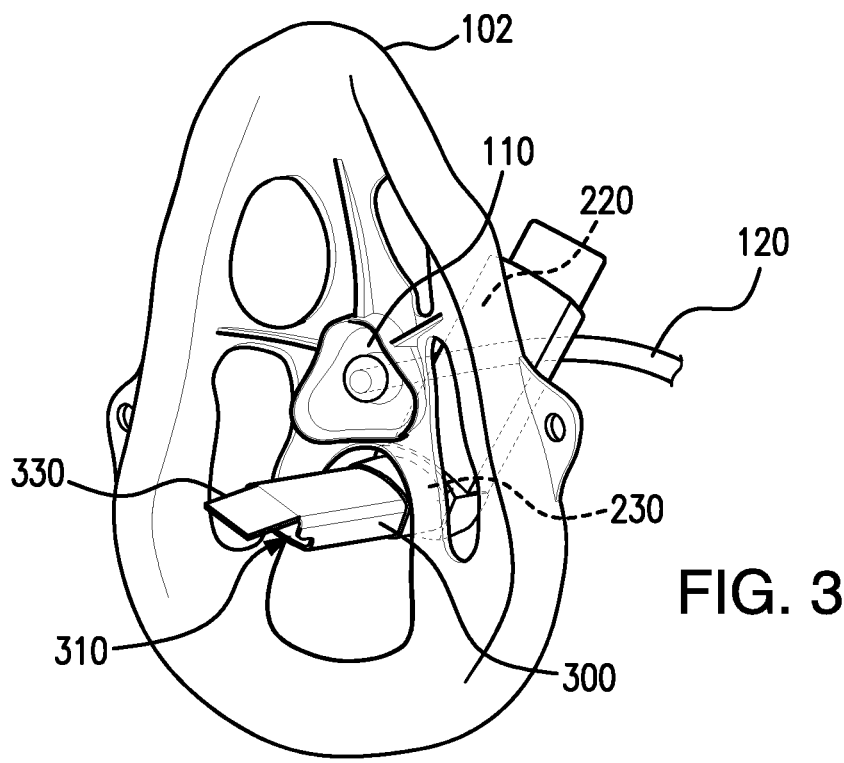
FIG. 3 is an perspective view of the inside of a "Southmedic OxyMask™ with a MDI with an extender tube according to this invention, ready for use.
Figure 4:
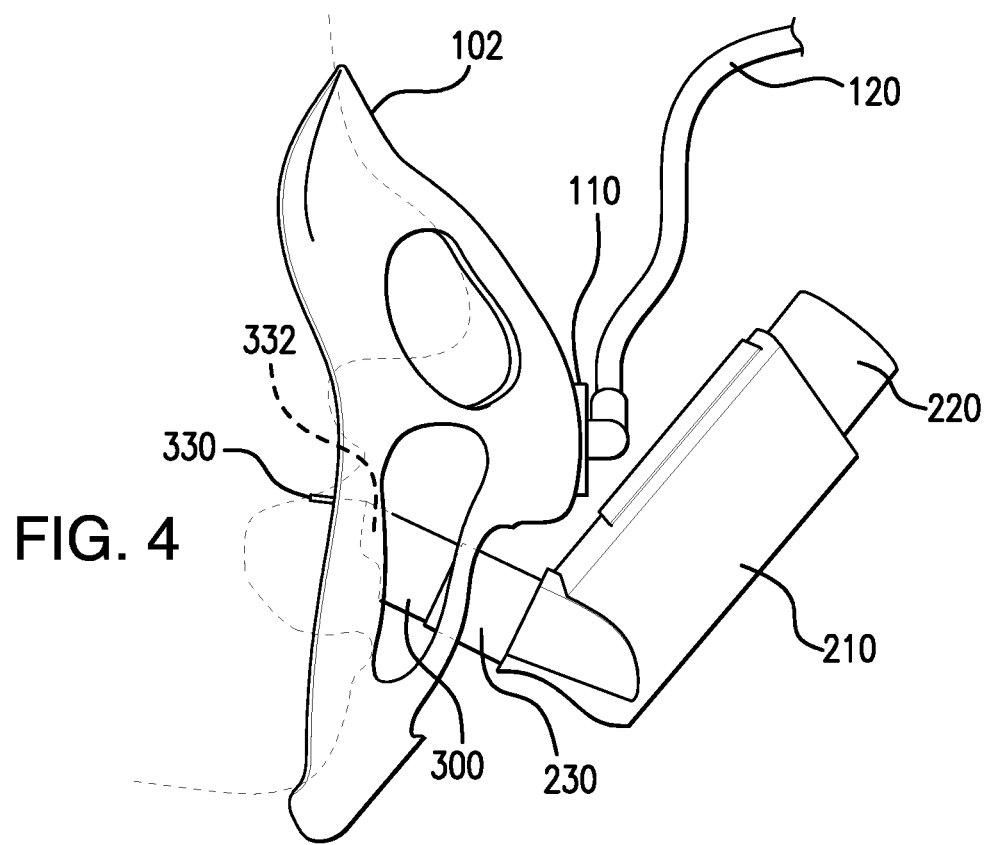
FIG. 4 is a side elevation view of a "Southmedic Oxy-Mask™ with an MDI with an extender tube according to this invention, ready for use.
Figure 14A:
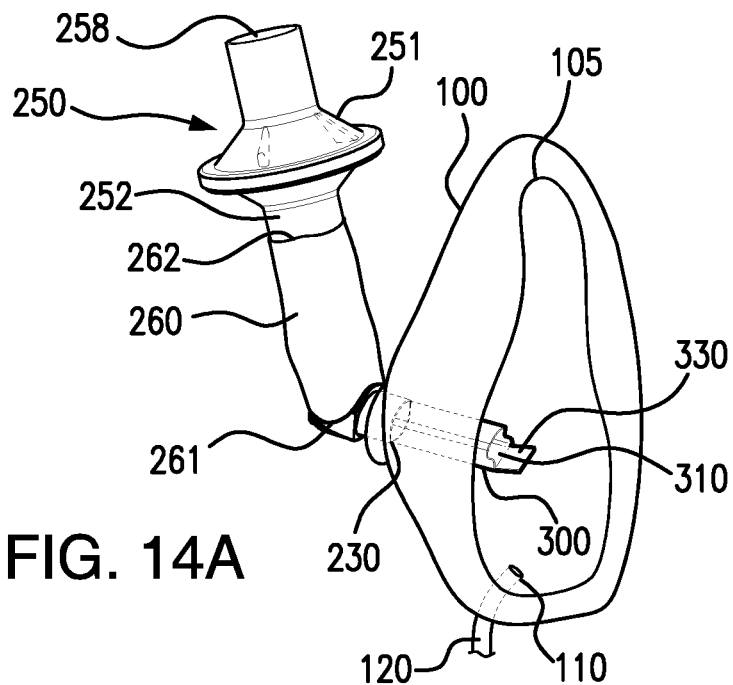
FIG. 14A is a perspective view of the apparatus according to an embodiment of the present invention, utilizing a CPR oxygen mask and having an exhalation filter.
Figure 14B:
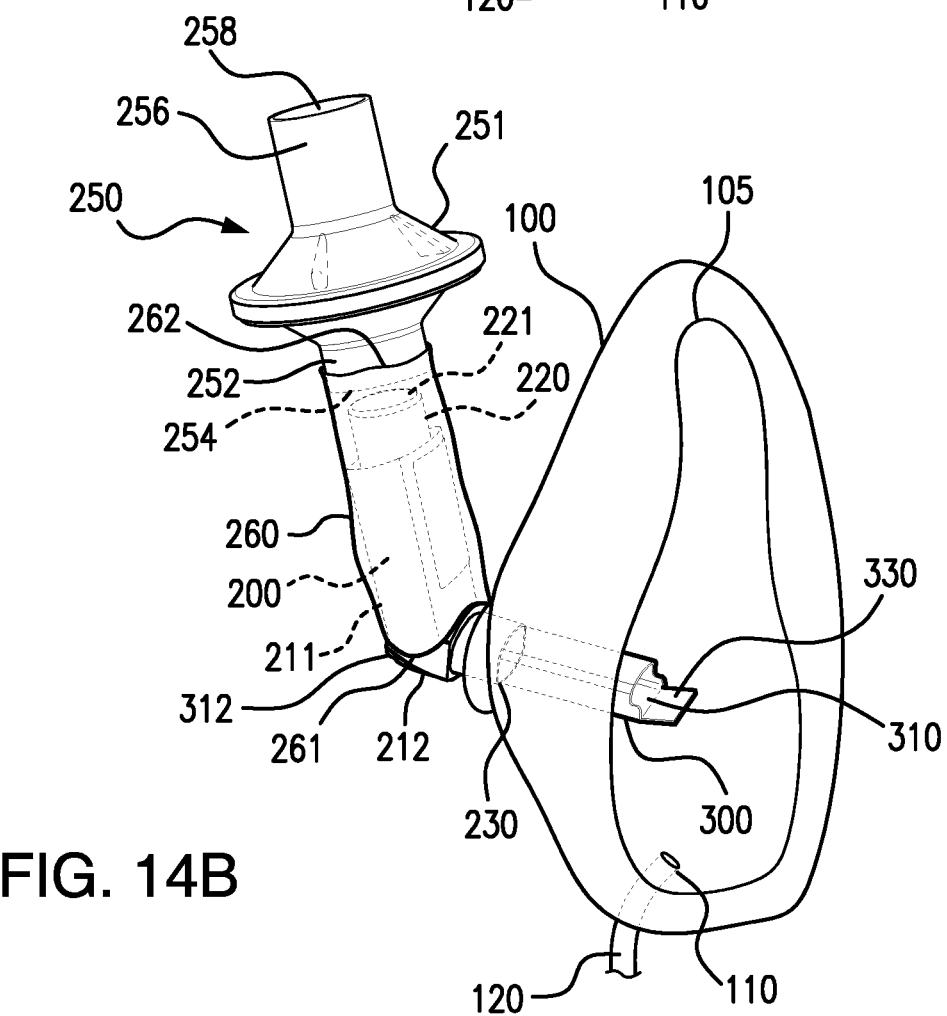
FIG. 14B is a detailed perspective view of the apparatus according to an embodiment of the present invention, utilizing a CPR oxygen mask and having an exhalation filter and showing the arrangement of the MDI canister and the filter.
Figure 15:
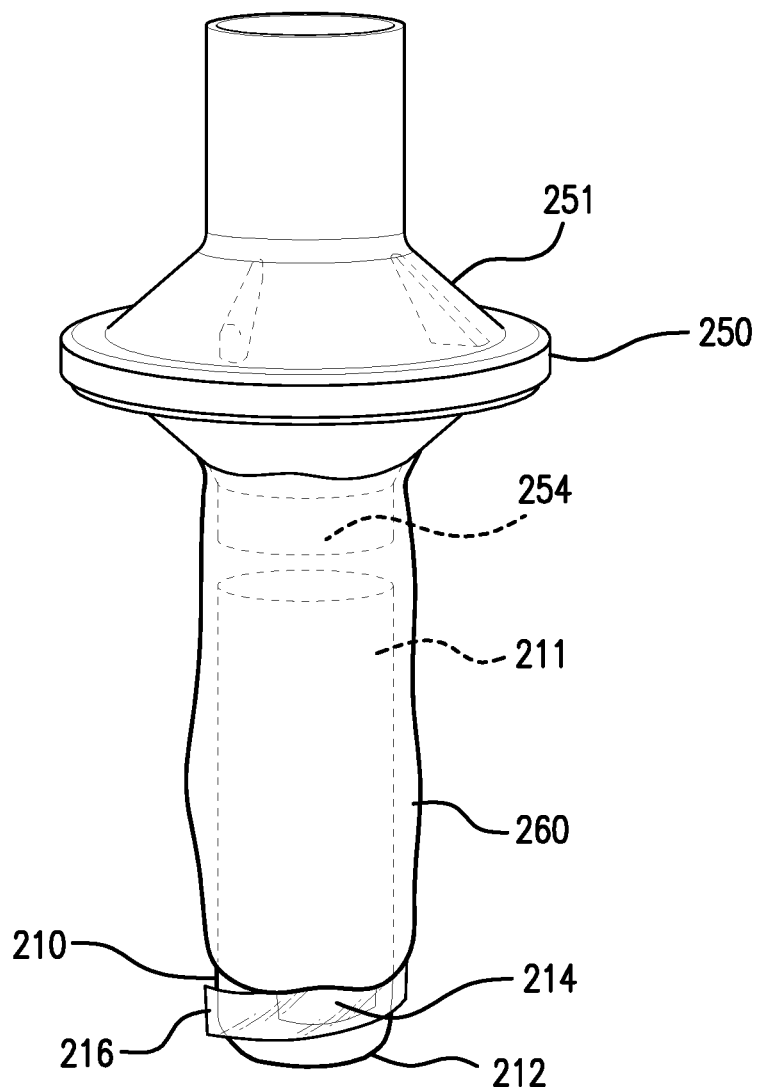
FIG. 15 is a perspective view of the rear of an MDI with a flexible sleeve and exhalation filter and counter window sealed airtight with clear tape.

FIGS. 8A and 8B are side views of two configurations of this invention. In FIG. 8A, flap 330 is on the bottom of the extender tube. In FIG. 8B, flap 330 is on the top of the extender. Since the flap 330 can direct the plume of aerosol medication up or down, the configuration employed in any particular situation depends on the angle of the extender tube relative to the mouth of the patient. The alteration of the plume direction is shown in FIG. 13, showing plume 500 directed away from flap 330. If the extender tube needs to be aimed downward, as illustrated in FIG. 2, then flap 330 should be on the bottom to direct the plume into the patient's mouth. FIGS. 3-5 show another embodiment in which the extender tube must be aimed upwards, so the flap 330 is positioned on the upper side to direct the plume slightly downward into the open mouth of the patient 400. In all cases, flexion of the flap is accomplished by pressing it against the patient's lip.

FIG. 9 is a top perspective view of the extender inserted into an MDI apparatus 200 with the flap on the bottom as in FIG. 8A. The drug canister is 200. The MDI body is 210. Distal end 310 shows the profile (332) of extender 300 with deflection flap 330 that may be flexed against the patient's lower lip to help direct the flow of the aerosol medication into the open mouth of the patient.

A further advantage to extender 300 is that it will tend to collimate the plume of aerosol from the MDI. Larger particles of drug, which tend to be on the periphery of the plume, will tend to impact the inside wall of the extender and stick there. These larger particles are undesirable. In the absence of a means of trapping these larger particles, they would tend to stick in the throat of the patient, and not deliver drug to the lungs. These larger particles of drug that impact the oral and pharyngeal areas can cause localized irritations and may be absorbed into the bloodstream and create unwanted side effects. It is therefore desirable to limit drug impacting and sticking to the throat. In the case of inhaled corticosteroids, local adverse effects may also occur.

In an embodiment of this invention according the FIGS. 1 and 2, the inventive apparatus includes a CPR oxygen mask 100 with rim 105 for covering the nasal and oral openings of a patient 400, having a ventral and dorsal surface and a 22 mm opening 140, adapted to host a removable air valve (not shown), attached to the dorsal surface of the mask 100. A metered dose inhaler 200 having body 210 and MDI canister 220, an extender tube 300 can be inserted into the opening 140 as shown. An oxygen inlet 110 with a PVC plastic connector tube 120 for the supply of oxygen from an external source into the mask may be provided. With MDI 200 inserted in the mask, the exhalation flow is through the body 200 of the MDI. There is sufficient clearance between the interior of MDI body 210, the trigger mechanism for the MDI (not shown), and MDI canister 220 for efficient exhalation. The masks 100 commonly include a strap 130 for securing the mask in position.

In an embodiment, this type of mask (termed herein a "CPR oxygen mask") is commonly used by first responders and EMS personnel for treatment of persons in the field in need of emergency respiratory therapy, such as from asthma, smoke inhalation, chronic obstructive pulmonary disease, accidents, trauma, respiratory arrest, and other conditions that can compromise adequate breathing or oxygenation. A marketed example of such a mask is the Ambu® Res-Cue Mask. This type of mask has a one-way valve for rescue breathing and an oxygen inlet, is inexpensive, and may be disposable or reusable. The one-way valve allows air to enter the mask from ambient during inhalation or rescue breaths from a person blowing into it. In addition, if a person is administering first-aid by blowing into the mask, the valve limits the exposure of patient's exhaled air and bodily fluids to the first-aid provider. Alternatively, a bag-valve ventilator can be used instead in the one-way valve port. With either the mouth-to-mask type resuscitation or bag valve, usually pressurized oxygen is a superior method for inadequate breathing when it is available.

There is a considerable degree of structural flexibility in these CPR oxygen masks with an air valve. Moreover, in many implementations, the air valve can be easily removed, by simply pulling it out with fingers. This can be done routinely, for example to change the valve for another use. The air valve utilizes an approximately 22 mm internal diameter opening (also termed herein a porthole) 140 in the mask body.

When the removable valve is removed from mask 100, the MDI mouthpiece 230 with the extender tube 300 pre-inserted into it may be inserted into the opening 140 from the dorsal surface of the mask 100 protruding about 3 cm into the CPR-oxygen mask.

The dorsal surface of the mask is sufficiently flexible to allow the extender to be tilted up or down relative to the patient's mouth. The objective is to position the distal end of the extender tube (310) just inside the open mouth of the patient, as shown by 410 in FIG. 2.

A typical set up of the MDI, CPR oxygen mask, and oxygen inlet on a patient is shown in FIG. 2. The MDI apparatus 200 includes drug canister 220, MDI body 210, and mouthpiece 230. The inventive extender 300 is shown inserted in MDI mouthpiece 230. The mouthpiece 230 is shown inserted into a 22 mm diameter opening 140 of the mask 100 after the one-way valve has been removed. Mask 100 is depicted with rim 105 covering the mouth and nose of the patient. Head strap 130 is also depicted. Oxygen nipple 110 is connected to tube 120 that is connected to a regulated pressurized oxygen supply. Patient 400 is shown with open mouth typical of an asthma attack 410.

In an embodiment, the extender tube 300 and MDI are assembled prior to insertion of the extender tube into the mask. In an embodiment, the mouthpiece of the MDI is inserted into the porthole in the mask, with the extender tube projecting into the interior of the mask, towards the mouth of the patient.

In an embodiment, an exhalation filter 250 may be fitted to the MDI with a flexible airtight sleeve, as depicted in FIGS. 14A, 14B, and 15. The exhalation filter can trap bacterial and viral particles and droplets bearing infectious agents in exhaled air to create a safer environment around the patient. There is sufficient clearance in and up the MDI boot to provide an efficient exhalation airway and carry exhaled air to the filter. In this embodiment, exhalation filter 250 in filter housing 251 is nested in sleeve 260. The exemplary embodiment employs a filter such as the Viro-Max™ bacterial-viral filter or a similar device available from Ventlab-SunMed and others. Such a filter has tubular connectors on either side of the filter housing. As shown in FIG. 14A, a proximal connector 252 is nested in distal end 262 of sleeve 260. The proximal end 261 of sleeve 260 fits over the upper body 211 of the MDI. The filter also has a distal tubular connector 256 that in this invention, is not connected to anything, open to ambient. The exhalation airway outlet to the atmosphere is 258.

In an embodiment, many MDI's have a counter window 214 in the back near the elbow as part of the actuation mechanism to show the number of doses remaining. If present, the counter window needs to be sealed, to prevent venting of exhaled air to the atmosphere, which would bypass the filter and defeat the purpose of the exhalation filter. A counter window can be sealed airtight with clear tape 216 to prevent leakage of exhaled breath, while maintaining the view of the counter.

In the embodiment of FIGS. 14A/14B/15, the sleeve 260 may be fabricated from a flexible rubber or other flexible material capable of maintaining its shape and elasticity. The sleeve must be flexible enough to allow the proximal edge of inlet 254 of the hard-plastic body of the filter to contact the MDI canister (220) by pushing the filter downward towards the MDI to trigger an actuation of the MDI. The sleeve must also be flexible enough to allow the filter housing to rebound on release to original position above the canister. The proximal edge 254 of the filter should, when seated in the sleeve, be positioned about 2-3 mm from the top 221 of MDI canister to allow enough room for patient's exhaled breath to pass thru to the filter 220. To actuate the MDI, the filter housing 251 is pushed down to contact the canister, 220 then further pushed down with it to cause an actuation of the MDI. The apparatus as described should be sufficiently flexible so that an MDI activation can be caused by pushing the filter housing 251 with fingers.

In operation, if oxygen is administered with a CPR oxygen mask, the one-way valve on the CPR mask can be used for rescue breathing or removed for bag-valve ventilation. The one-way valve can be removed in a few seconds with the fingers, and the MDI with extender can be inserted in the porthole of the mask in place of the valve. The MDI can be manipulated manually to direct the inventive extender tube 300 so that the distal opening 310 is just within the open mouth of the patient. As these masks are configured, the deflector flap 330 will be on bottom side of the extender tube with a CPR oxygen mask. Then the MDI can be activated by depressing its canister 220 to administer a dose of the medication as the patient is inhaling while oxygen is flowing, without interruption, through the oxygen inlet 110 into the mask at up to typical available 15 liters per minute flow.

As shown in FIG. 2, the extender 300 is aimed at the open mouth 410 of patient 400. This method does not require that the patient is conscious or competent (i.e., able to follow instructions) as long as the mouth is somewhat open, and MDI actuation is timed so that the patient inhales at approximately the same time as the actuation, to draw the aerosolized drug into the lungs.

The extender tube is specifically designed to not interfere with the mechanics of the inhaler. It can be inserted easily, but firmly and securely, into a standard aerosol MDI (e.g., Ventolin HFA®) mouthpiece and can be adapted to any MDI mouthpieces as needed. This includes MDI mouthpieces with other medications than albuterol (salbutamol outside the U.S.), including, Duolin HFA, Salbutral AC HFA, Flovent HFA, formoterol, etc. As shown in FIG. 12, the extender tube may have notches 340 on the proximal end. The notches 340 may be necessary to avoid the mechanism of the inhaler. The notches 340 may be provided on both top and bottom surfaces of the extender tube.

In an embodiment, the extender tube 300 may be a bright color, such as bright yellow, to give good visual contrast as seen thru the mask, so that a responder can maneuver the distal end of the extender tube 310 to a position just within the mouth. The flexibility of a plastic CPR oxygen mask body with its 22 mm opening and the mask clarity, along with a bright yellow color of the extender, allow the extender to be readily visualized and aimed at and into the open mouth of the patient during observed tidal inhalation or hyperventilation during an episode of breathlessness, e.g. asthma, by the person administering the aerosol.

The inventive extender also solves the problem, observed by the inventors, of dispersion of drug aerosol particles in an uncontrolled fashion on the interior of the mask when simply inserting an MDI into the 22 mm one-way valve port in an oxygen mask. With the inventive extender tube 300, the oxygen jet entering the mask is diverted around (blocked off from) the aerosol plume from the MDI, and it puts the plume just inside the mouth, thus ensuring efficient aerosol delivery into the open mouth and virtually eliminating dispersion of the aerosol by the incoming oxygen jet.

Two alternative mask embodiments are shown in FIGS. 3-7. FIGS. 3-5 show the use of the inventive device with a Southmedic "OxyMask™", a type of mask with large perforations and an oxygen jet in the center of the mask. In normal use, the oxygen jet is aimed at the mouth and nose of the patient. This mask has many desirable attributes and is preferred by many physicians and respiratory therapists. Many patients find it less confining than other masks. The inventive MDI with an extender tube can be manually inserted into the large perforation at the bottom of the mask and the extender tube can be easily aimed toward the mouth of the patient. The MDI would have to be supported by a person's hand while using this type of mask. The extender tube is directed at and just into the open mouth of the patient and the MDI is actuated when the patient inhales. Because of the location of the large perforation on the bottom, the extender tube will have to be aimed upward. Flap 330 should therefore be positioned on the top of the extender tube as in FIG. 8B to help direct the flow of the aerosol slightly downward into the mouth of the patient.

Figure 6:
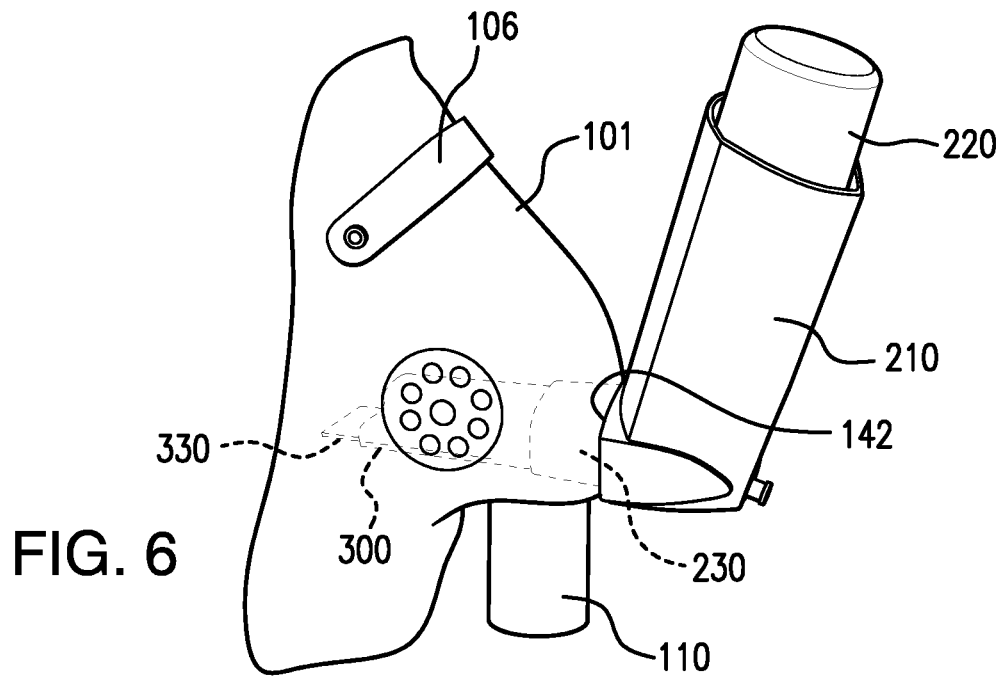
FIG. 6 is a side elevation view of a rebreather mask with a MDI with an extender tube according to this invention inserted in a perforation therein.
Figure 7:
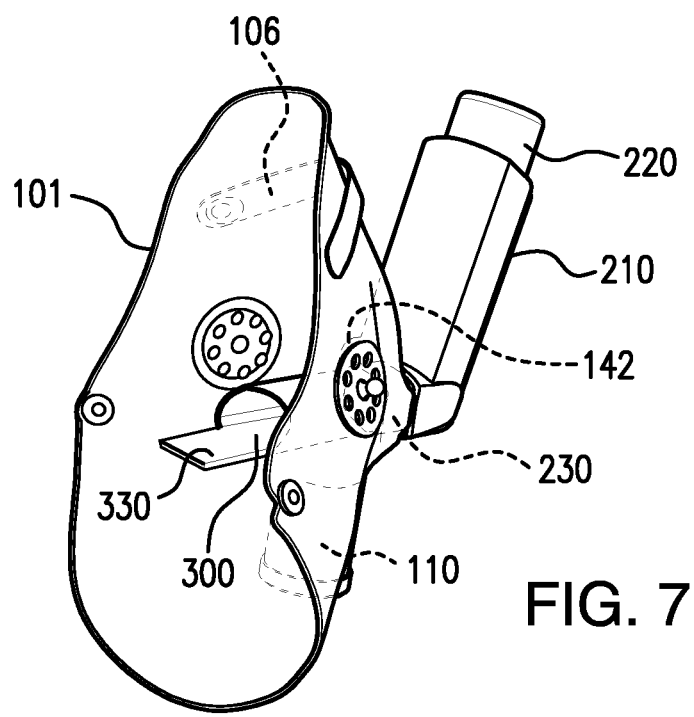
FIG. 7 is a perspective view from the side and viewing the interior of a transparent rebreather mask with a MDI with an extender tube according to this invention inserted in a perforation therein.

FIGS. 6-7 show an embodiment using an alternative and inexpensive oxygen mask style. This type of mask (termed herein a "rebreather mask" or a "non-rebreather mask") (101) has an oxygen inlet 110 pointed downward. These masks also typically have a nose bridge 106 of flexible metal to give the mask a snug fit. These masks do not include a one-way valve or perforation since not intended for CPR rescue breathing. A rebreather or non-rebreather mask for use with this invention would have to be made available with a punch-out section so that an MDI mouthpiece with extender tube can be inserted into an opening 142 (also termed herein a "porthole") that would be created if the punch out was made.

The inventors carried out 25, N=1 experiments administering 6-12 puffs×90 mcg each of albuterol HFA (salbutamol) during normal tidal breathing, timed to inhalation, with a CPR-oxygen delivery mask and an OxyMask using the MDI-extender at 0-25 LPM oxygen flow range. In almost all cases the patient clearly experienced typical mild beta-agonist adverse effects (Tmax plasma albuterol at 25 min=2-3 ng/mL) representing pulmonary/LRT absorption and lasting a little more than 4 hours (due to later non-lung systemic absorption). The plasma albuterol was, as expected (extrapolating from the symptoms over 0-4 hours), adequately high (2-3 ng/mL at 25 min) for effective treatment of severe bronchospasm. These results are similar to those reported in the Ventolin HFA package insert (Pharmacokinetics Sec. 12.3) reporting that 12 normal subjects given a 1,080 mcg dose of albuterol (i.e., 12×90 mcg puffs) from a Ventolin (albuterol) HFA inhaler. For most exacerbations 8-12 puffs of 90 mcg of albuterol (recommended in numerous national and international guidelines for therapy of acute exacerbations of asthma) would effectively relieve most acute exacerbations, as has been the case using VHCs. In addition, oxygen concentration as sampled in-mouth by a Maxtec® OM-25 oxygen analyzer was consistent with expected for the oxygen flow rate, and unaffected by the albuterol HFA administration at the various flow rates tested ranging from 0-25 LPM.

The inventors believe that the inventive extender 300 can collimate the aerosolized drug on its way to the mouth, while at the same time removing larger non-respirable particles which are known to mainly occupy the aerosol plume periphery. This may add to the efficiency and safety of aerosol delivery because it is capable of directing the aerosol into the open mouth if the MDI boot with extender is tilted appropriately by the individual providing the therapy, and by removing aerosol that is ineffective for the lungs and may otherwise cause side effects.

The inventive method may have an advantage of speed as compared to SVN's. When a patient presents in respiratory distress, one objective of treatment may be getting a bronchodilator drug into the patient's lungs as rapidly as possible. However, an SVN (which can administer drug and oxygen simultaneously as with this invention) takes several minutes to set up and this may be further delayed if a respiratory therapist needs to be summoned to do it. Moreover, the oxygen flow with an SVN is relatively fixed in a narrow range which may be too low or too high for the patient's needs, and it cannot be adjusted out of this range without adversely effecting aerosol delivery. The inventive device is almost immediately ready (30-60 seconds) to provide oxygen and aerosol medication. It is ready to use as stored. As a comparative example, an SVN may be in an ambulance, but is unlikely to be carried by EMS personnel into a building where a person in respiratory distress may be located. Thus, with only an SVN available for aerosol plus oxygen together in the ambulance, EMS personnel may need to transport a patient in distress from the scene to the ambulance while only receiving oxygen, before initiating both therapies by switching to the SVN in the ambulance. With the invention, set up is much quicker (a few seconds since stored ready to use) and does not require measuring a liquid drug into a reservoir as with an SVN. The invention can be easily carried to a patient in distress, rather than the converse, thus starting bronchodilator treatment right at the scene and eliminating the need to switch delivery devices when back in the ambulance.

| Legend for the drawings | |
|---|---|
| 100 | CPR oxygen mask with one-way valve orifice and oxygen inlet |
| 101 | Simple oxygen mask |
| 102 | Southmedic OxyMask ™ |
| 105 | Rim of mask |
| 106 | Nose plate |
| 110 | Oxygen inlet |
| 120 | Oxygen tube |
| 130 | Head strap |
| 140 | Orifice (porthole) for one-way valve |
| 142 | Orifice for MDI in rebreather mask. |
| 200 | MDI assembly |
| 210 | MDI body |
| 211 | MDI upper body |
| 212 | MDI elbow |
| 214 | MDI Counter window |
| 216 | Clear tape strip providing an air seal over the counter window. |
| 220 | MDI canister |
| 221 | MDI canister top |
| 230 | MDI mouthpiece |
| 250 | Exhalation filter |
| 251 | Filter housing |
| 252 | Proximal inlet tube |
| 254 | Proximal inlet tube on filter |
| 256 | Distal outlet tube |
| 258 | Distal air outlet |
| 260 | Flexible sleeve |
| 261 | Proximal end of sleeve |
| 262 | Distal end of the sleeve |
| 300 | Extender tube |
| 310 | distal opening of extender tube |
| 320 | proximal end of extender tube inserted into MDI mouthpiece |
| 330 | Deflector flap |
| 332 | Scoop (Lip) on distal end of extender tube |
| 340 | Proximal notches |
| 400 | Patient |
| 410 | Mouth of patient |
| 500 | Plume of aerosol deflected by flap 330 |

The invention claimed is:

1. An apparatus for administering an inhaled medication to a patient (400) with an open mouth, wherein the medication is administered from a pressurized metered dose inhaler (MDI) (200) having a canister (220) containing an inhalable medication; and an oxygen delivery mask (100, 101) configured to cover the nose and mouth of the patient, wherein the oxygen mask provides medical oxygen at a flow rate up to 15 liters per minute, wherein the oxygen mask has an approximately 22 mm diameter opening (140) on a dorsal surface of the mask; wherein the improvement comprises:
   an extender tube (300) 3-10 cm long having a proximal end (320) that fits into or over a mouthpiece (230) of the MDI, wherein the extender tube and the MDI mouthpiece are inserted into the 22 mm opening of the mask to a position such that a distal end (310) of the extender tube is just inside the open mouth of the patient; and
   wherein an actuation of the MDI administers a dose of the inhalable medication to the patient while oxygen remains flowing without interruption at up to about 15 liters per minute flow rate.

2. The apparatus of claim 1 wherein the mask has an air valve in the 22 mm opening, and wherein the air valve is removed and the MDI mouthpiece with the extender tube is inserted into the 22 mm opening, and the MDI is actuated to deliver one or more doses of the medication to the patient.

3. The apparatus of claim 1 wherein the mask has an approximately 22 mm porthole that is vacated to provide an opening for the MDI mouthpiece with extender inserted within it, and wherein the MDI with the extender tube is inserted into the 22 mm opening, and the MDI is actuated to deliver one or more doses of the medication to the patient.

4. The apparatus of claim 1 further comprising an exhalation filter (250) that traps infectious agents, wherein the filter is nested in a distal end of a flexible sleeve (260), such that an exhalation airway is created through the MDI body (210) and the exhaled air from the patient passes through the exhalation filter.

5. The apparatus of claim 1 further comprising an exhalation filter (250) in a housing nested in a distal end of a flexible sleeve (260), wherein a proximal end (261) of the flexible sleeve is nested over an upper body (211) of the MDI, wherein the exhalation filter housing is pushed towards the canister in the MDI to actuate the MDI.

6. The apparatus of claim 1, wherein the extender tube is 5-6 cm long.

7. The apparatus of claim 1, wherein the distal end of the extender tube is further equipped with a flexible flap that can direct a flow of the aerosolized medication in a non-linear direction upon exit of the aerosolized medication from the distal end of the tube.

8. The apparatus of claim 1, wherein the medication is administered at a scene of an emergency not in a hospital.

9. An apparatus for administering an inhaled medication to a patient (400) with an open mouth, wherein the medication is administered from a pressurized metered dose inhaler (MDI) (200) having a canister (220) containing an inhalable medication; and an oxygen delivery mask (102) with a rim configured to cover the nose and mouth of the patient, wherein the mask has a plurality of openings and an oxygen inlet in a midline location, and wherein the oxygen mask provides medical oxygen at a flow rate up to 15 liters per minute; wherein the improvement comprises an extender tube (300) approximately 6 cm long is provided having a proximal end (320) that fits into a mouthpiece (230) of the MDI;

wherein the extender tube and the MDI mouthpiece are inserted into an opening in the mask such that a distal end (310) of the extender tube is configured to be positioned just inside the open mouth of the patient; and wherein an actuation of the MDI administers a dose of the inhalable medication to the patient while oxygen remains flowing without interruption at up to 15 liters per minute flow rate.

* * * * *